Nov. 28, 1950 H. C. SWIM Plant Pat. 994
ROSE PLANT
Original Filed March 11, 1947
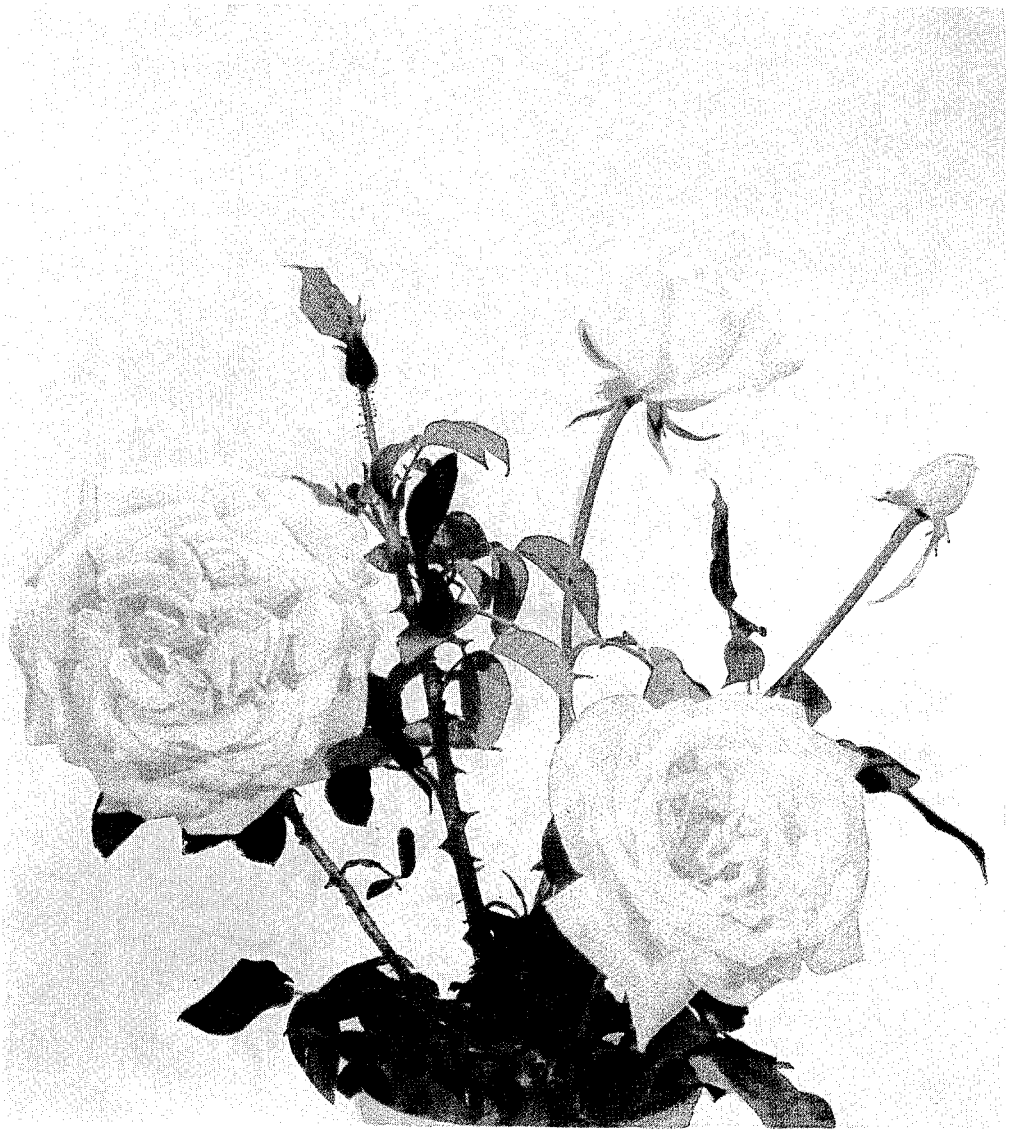
Inventor
H. C. Swim
By Robb & Robb
Attorneys Patented Nov. 28, 1950 Plant Pat. 994

UNITED STATES PATENT OFFICE

994

ROSE PLANT

Herbert C. Swim, Ontario, Calif., assignor, by mesne assignments, to Eldon Pinkeney Dering, doing business under the name and style of Peterson & Dering, Scappoose, Oreg.

Substituted for abandoned application Serial No. 733,887, March 11, 1947. This application filed July 17, 1950, Serial No. 174,350

1 Claim. (Cl. 47—61)

This application constitutes a substitute for my previous application Serial No. 733,887, originally filed March 11, 1947, and which was allowed March 31, 1948, but which application was abandoned.

The invention relates to a new and distinct variety of rose plant, characterized as to novelty by a combination of characteristics which make it distinct from all other varieties of roses introduced to commerce.

In carrying out my objective, I crossed two well established varieties of roses, "Charlotte Armstrong" (Pl. Pat. #445) and "Times Square" (unpatented). The result of this breeding has produced a variety which includes the following dominant combination characteristics:

(1) The strongest damask fragrance to my knowledge in hybrid tea roses and more particularly in roses of this class in the pink-color range.

(2) Very long, strong stems bearing an individual flower of exhibition size on each stem.

(3) A combination of form, size, and color in the flower unique in hybrid tea roses.

(4) A heavy, leathery, highly mildew-resistant foliage of moderately large size.

(5) A plant characteristic of branching very little at the base of the plant, but with stems and flowers borne more or less continuously at a progressively greater height during each growing season.

Not only do these distinctions hold as regards other known varieties generally, but they apply equally as well relative to the parents of the new variety. While it shows definite evidence of inheritance traits from one or the other of its parents, the recombination of characters in this new variety and the expression of some which are recessive in its parents and the expression of intermediacy between the two parents in other characters, leaves this new variety with very remote resemblance to either parent.

More specifically, while it slightly resembles "Charlotte Armstrong" in the type of thorn pattern, the shape of the thorns does not resemble that of "Charlotte Armstrong." There is some slight resemblance in the opening bud and newly opened flower of this new variety to the corresponding stages in the flower of "Charlotte Armstrong," but the resemblance is not at all marked for actually it is more accurate to say that the form of these two stages of the flower in this new variety is more intermediate between the two parents. This new variety has definitely inherited the mildew resistance of "Charlotte Armstrong" and to some extent, the texture of the individual leaf. The shape of its leaves and leaflets is again intermediate between the parents also. The habit of growth is distinct from that of either parent and this new variety is taller growing and with longer stems than either parent. The fragrance of the flower of this new variety is far superior to that of either parent and represents an expression of a recessive trait carried in both parents but expressed in neither of them.

This new variety represents the successful attainment of my effort to produce a rose with the combination of maximum fragrance of flower produced on a very long-stemmed, vigorous mildew-resistant plant.

Asexual reproduction of this new variety by budding at Ontario, California, shows the foregoing characteristics come true to form and are established.

In the drawing, specimens of the new variety are shown, with the blooms at different stages from bud to full blown flowers, and the foliage in different stages of development.

The following is a detailed description of the new variety, color terminology being in accordance with Robert F. Wilson's Horticultural Colour Chart with exceptions noted from Ridgway's Color Standards and Nomenclature:

Type: Hardiness untested; tall; bush; outdoor; seedling; for cut flowers and garden decoration.

Class: Hybrid tea.

Breeding: Seedling.

*Seed parent.*—"Charlotte Armstrong."

*Pollen parent.*—"Times Square."

Propagation: Holds its distinguishing characteristics through succeeding propagations by budding.

*Flower*

Locality where grown: Ontario, California.

Flowers borne: Singly to stem; on strong, very long stems.

Quantity of bloom: Moderate; outdoors.

Continuity: More or less continuous during growing season.

Fragrance: Very strong; Damask.

Bud:

*Peduncle.*—Long; heavy; bending to erect; medium rough; numerous, gland-tipped cilia and prickles. Color—Absinthe Green, Plate XXXI (Ridgway).

*Before calyx breaks.*—Size—medium to large. Form—long; pointed to ovoid, often with a conspicuous neck; with foliaceous appendages, tomentum and gland-tipped cilia on the surface of the bud; with slender, much cut foliaceous parts extending beyond the tip of the bud equal to ¾ or more of its length.

*As calyx breaks.*—Color—near Chartreuse Green, Plate 663/2, page 90, at base gradually becoming Carmine Rose, Plate 621/1, page 75, toward apex.

*Sepals.*—Inner surface with fine, woolly tomentum. When the margin of a sepal is not covered by the margin of an adjacent sepal, it has tomentum and stipitate glands. If margin is covered with adjacent sepal it has only woolly tomentum.

*As first petal opens.*—Size—large. Form—long; pointed. Color—outside—French Rose, Plate 520, page 136, from apex to just below center of petal, becoming Carmine Rose, Plate 621/2, page 75, at margin of petal with a blotch of Amber Yellow, Plate 505, page 132, at base of petal. Inside—Neyron Rose, Plate 623/1, page 76, with a blotch of Buttercup Yellow, Plate 5/1, page 5, at base of petal.

*Opening.*—It is retarded, occasionally prevented from opening by cold, wet weather.

Bloom: Size, when fully open—large; 4½ inches to 5½ inches.

*Petalage.*—Double; from 35 to 50 petals plus 3 to 5 petaloids; arranged regularly.

*Form.*—Cupped at first; becoming open; petals at first loosely rolled outward; becoming later, at maturity, somewhat more tightly rolled outward at apex.

Petals: Soft; with inside satiny and outside shiny.

*Shape.*—Outside—broadly obovate with apex rounded. Intermediate—obovate with apex rounded. Inside—obovate with apex rounded.

*Color.*—Colors may be modified by being washed with other colors.

This description of a newly opened flower was made from a rose grown outdoors in the month of October, at Ontario, California:

*Color.*—*Outside petal*—outside surface: near French Rose, Plate 520/2, page 136, from apex to just below center of petal, becoming Rhodamine Pink, Plate 527/2, page 138, at margin of petal, with base of petal Amber Yellow, Plate 505/1, page 132; inside surface: Rhodamine Pink, Plate 527/1, page 138, with a blotch of Lemon Yellow, Plate 4/2, page 4, at base of petal. *Intermediate petal*—outside surface: base of petal near Amber Yellow, Plate 505, page 132, gradually becoming near Rhodamine Pink, Plate 527/2, page 138; inside surface: Rhodamine Pink, Plate 527/1, page 138, with a blotch of Lemon Yellow, Plate 4/2, page 4, at base of petal. *Inner petal*—outside surface: Rhodamine Pink, Plate 527/2, page 138, with a blotch of Lemon Yellow, Plate 4/2, page 4, at base of petal; inside surface—Rhodamine Pink, Plate 527/1, page 138, with a blotch of Lemon Yellow, Plate 4/2, page 4, at base of petal.

This description was made from a rose that was open for three days outdoors in the month of October, at Ontario, California:

*Color.*—*Outside petal*—outside surface: Shell Pink, Plate 516/3, page 135, from apex to just below center of petal, becoming Rhodamine Pink, Plate 527–3, page 138, at margin, with base of petal Naples Yellow, Plate 403/3, page 121; inside surface: Between Rhodamine Pink, Plate 527/2, page 138, and Rhodamine Pink, Plate 527/3, page 138, with a blotch of Aureolin, Plate 3/3, page 3, at base of petal. *Inside petal*—Outside surface: Base of petal near Naples Yellow, Plate 403/2, page 121, gradually becoming Rhodamine Pink, Plate 527/2, page 138; inside surface: near Rhodamine Pink, Plate 527/2, page 138, with a blotch of Aureolin, Plate 3/2, page 3, at base of petal.

*General color effect.*—Newly opened flower—between Rhodamine Pink, Plate 527–2, page 138, and Rhodamine Pink, Plate 527/1, page 138. Three days open—between Rhodamine Pink, Plate 527/3, page 138, and Rhodamine Pink, Plate 527/2, page 138.

*Behavior.*—Drop off cleanly; fading from Rhodamine Pink, Plate 527/1, page 138, to Rhodamine Pink, Plate 527/3, page 138.

*Flower longevity.*—On bush in garden—3 to 4 days in October. Cut roses grown outdoors kept at living-room temperatures, 2 to 3 days in October.

*Reproductive organs*

Stamens: Many; arranged irregularly about pistils; mixed with few petaloids.

Filaments: Medium to long; 5 to 12 mm. in length. Color—Nasturtium Red, Plate 14/2, page 14, gradually becoming Straw Yellow, Plate 604/1, page 67, near anthers. Most with anthers.

Anthers: Medium size; all open approximately at once. Color—near Straw Yellow, Plate 604/1, page 67.

Pollen: Moderate. Color—near Indian Yellow, Plate 6/1, page 6.

Pistils: Many.

Styles: Uneven; medium length; average caliper; loosely bunched. Color—Uranium Green, Plate 63/3, page 63, at base, gradually becoming Carmine, Plate 21, page 21, near stigma.

Stigma: Pinkish-white; somewhat translucent.

Hips: This variety seldom sets seed under normal growing conditions.

Foliage:

*Leaves.*—Compound of 5 to 7 leaflets; moderately sparse; moderately large; leathery; surface dull.

*Leaflets.*—Ovate with apex acute; base obtuse; margin doubly serrate. Color—mature—upper surface: Cress Green, Plate XXXI (Ridgway); under surface: Between Deep Chrysolite Green, Plate XXXI (Ridgway), and Rainette Green, Plate XXXI (Ridgway). Young—upper surface: near Light Cress Green, Plate XXXI (Ridgway), washed with Dark Mineral Red, Plate XXVII (Ridgway); under surface: Deep Chrysolite Green, Plate XXXI (Ridgway), washed with Mineral Red, Plate XXVII (Ridgway).

*Rachis.*—Medium heavy. Upper side grooved with many stipitate glands; under side moderately prickly and with many stipitate glands.

*Stipules.*—Medium to long; medium width; with medium long points turning out at an angle of more than 45°, usually recurved toward the stem.

*Disease.*—Resistant to mildew.

Growth:

*Habit.*—Upright spreading; little branched particularly at base.

*Growth.*—Vigorous.

*Canes.*—Heavy.

*Main stems.*—Rainette Green, Plate XXXI (Ridgway). *Large prickles*—many; medium to long; slightly hooked downward; with broad base. Color—near Vandyke Brown, Plate XXVIII (Ridgway) blotched with Bone Brown, Plate XL (Ridgway). *Small prickles*—several; near Vandyke Brown, Plate XXVIII (Ridgway) blotched with Bone Brown, Plate XL (Ridgway). *Hairs*—none.

*Branches.*—Deep Chrysolite Green, Plate XXXI (Ridgway). *Large prickles*—several; medium length; slightly hooked downward; with moderately broad base; Sayal Brown, Plate XXIX (Ridgway). *Small prickles*—several; Sayal Brown, Plate XXIX (Ridgway). *Hairs*—none.

*New shoots.*—Near Asphodel Green, Plate XLI (Ridgway) slightly washed with Etruscan Red, Plate XXVII (Ridgway). *Large prickles*—several; average length; slightly hooked downward; with moderately broad base; apex near Deep Sea-foam Green, Plate XXXI (Ridgway), gradually becoming washed with Etruscan Red, Plate XXVII (Ridgway). *Small prickles*—several; apex near Deep Sea-foam Green, Plate XXXI (Ridgway), gradually becoming washed with Etruscan Red, Plate XXVII (Ridgway) toward base. *Hairs*—none; several stipitate glands.

I claim:

A new and distinct variety of rose plant characterized as to novelty by the strong fragrance of its flowers; the very long, strong stems bearing individual flowers of exhibition size on each stem; a combination of form, size and color in the flower unique in hybrid tea roses; the heavy, leathery, highly mildew-resistant foliage of moderately large size; and by its habit of vigorous growth to a tall plant with very little branching at the base, but with stems and flowers borne more or less continuously at a progressively greater height during each growing season, substantially as shown and described.

HERBERT C. SWIM.

No references cited.